United States Patent [19]

Hayashi et al.

[11] Patent Number: 4,559,172

[45] Date of Patent: Dec. 17, 1985

[54] PROCESS FOR ACYLATION WITH NOVEL ACYLATING AGENT

[75] Inventors: Ikuo Hayashi, Koriyama; Keizo Ogihara, Sukagawa; Tadao Itikawa, Fukushima; Kiyoshi Shimizu, Koriyama, all of Japan

[73] Assignee: Nitto Boseki, Fukushima, Japan

[21] Appl. No.: 605,781

[22] Filed: May 1, 1984

[30] Foreign Application Priority Data

May 4, 1983 [JP] Japan .................................. 58-78572

[51] Int. Cl.$^4$ .................... C07C 103/52; C07C 79/46; C07C 125/06; C07C 67/02
[52] U.S. Cl. .............................. 260/112.5 R; 560/22; 560/29; 560/92; 564/254; 564/185; 564/192
[58] Field of Search ................... 260/112.5 R; 560/22, 560/29, 92; 564/254, 185, 192

[56] References Cited

PUBLICATIONS

Chem. Pharm. Bull., 17, (9) 1937–1941 (1969).
Liebigs, Ann. Chem., 677, 185–190 (1964).
Chem. Abstr., vol. 100, (1984) 7101a.
Chem. Abstr., vol. 100, (1984) 68713y.

*Primary Examiner*—Delbert R. Phillips
*Attorney, Agent, or Firm*—Bert J. Lewen; Henry Sternberg

[57] ABSTRACT

This invention relates to a novel acylation process which comprises using as the acylating agent an o-hydroxy-substituted aromatic oxime ester represented by the general formula (I)

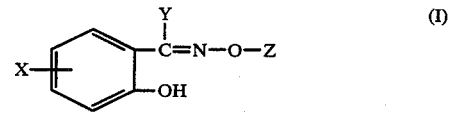

and mixing said acylating agent with an amine substance represented by the general formula (III)

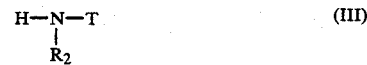

to form a compound represented by the general formula (IV)

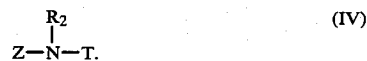

9 Claims, No Drawings

PROCESS FOR ACYLATION WITH NOVEL ACYLATING AGENT

This invention relates to a process which comprises mixing and reacting an oxime-type acylating agent (I) with a compound (III) to be acylated to form an acylated compound (IV), said compounds (I), (III) and (IV) being as specified in the appended claim 1.

It is a known fact that an oxime in the form of active ester can be used as an acylating agent in the field of peptide synthetic chemistry. More particularly, an aromatic or aliphatic aldoxime or ketoxime generally forms an ester (hereinafter referred to as active ester) by acting through its hydroxyimino group (—CY=N—OH) as alcohol component in the reaction with a carboxylic acid or the carboxylic acid component of an amino acid or peptide to produce a compound of the general formula (I). It is possible to combine this compound (I) through an amide linkage with a primary or secondary amine or the amine component (III) of another amino acid or peptide to synthesize a peptide or higher peptide (IV). The active ester of an oxime, however, is generally not sufficiently reactive and cannot be indepenently used as an acylating agent. As a means for improving the reactivity, there has been reported a method for activating an oxime ester by the addition of a weak acid such as acetic acid or formic acid as catalyst [M. Fujino and O. Nishimura, Chem. Pharm. Bull., 17, 1937 (1969)]. For instance, it is reported that when an active ester of acetophenone oxime or cyclohexanone oxime is used alone, 3 or 4 days are required for the completion of the reaction and, moreover, the yield is low [M. Fujino and O. Nishimura, Chem. Pharm. Bull., 17, 1937 (1969)].

Another means of improvement is the activation of hydroxyimino group itself. There is known a general rule for the activation such that the introduction, into the hydroxyimino group, of an electron attractive group such as, for example, nitro group, cyano group or carboxyl group favors the activation, whereas an electron donative group such as hydroxyl or acetyl group behaves in favor of inactivation. For instance, there is reported an attempt to enhance the activity of esters of acetophenone oxime, m-nitrobenzaldehyde oxime and m-nitroacetophenone oxime by introducing into the hydroxyimino group a highly electron attractive group such as phenyl or nitro group. The result showed some improvement compared with the ester of unsubstituted oxime [G. Losse et al., Justus Liebigs Ann. Chem., 677, 185 (1964)].

The aforementioned elaborated oxime esters, however, show a far lower reactivity than that of a p-nitrophenol ester widely used in the field of peptide synthetic chemistry.

The present inventors examined the reactivity of esters of various oximes and have found that a novel oxime ester of the general form (I) reacts very rapidly with a compound (III). As is apparent from its structural formula, the present compound of the general formula (I) has an electron donative hydroxyl group which has been considered to cause the inactivation nevertheless, the reactivity of the present compound (I) was found to be not only far higher than that of the conventional oxime ester but also comparable to or higher than that of a p-nitrophenol ester. It is a surprising fact that the presence of the hydroxyl group, which is an electron donative group, is most important in the method of this invention. General description of the procedure of acylation according to this invention is given below.

The adequate manner of employing the present acylating agent is as shown below.

The active oxime ester according to this invention is prepared by dissolving an N-protected amino acid or peptide and a corresponding oxime in a nonaqueous solvent such as tetrahydrofuran (THF), dioxane, dimethylformamide (DMF), or methylene chloride, cooling the resulting solution, adding dicyclohexylcarbodiimide to the cooled solution, allowing the reactants to react for several hours at 0° C. or below, then stirring the reaction mixture for several to 24 hours at room temperature, then removing the precipitated dicyclohexylurea by filtration, partitioning the filtrate between water and ethyl acetate, separating the organic layer, washing the organic layer successively with 5-% aqueous citric acid solution, 1-N aqueous sodium hydrogen carbonate solution and water (the washing with the aqueous sodium hydrogen carbonate solution is unnecessary in the case of 5-nitro-2-hydroxyoxime), drying the washed organic layer over magnesium sulfate, removing the solvent by distillation, and recrystallizing the residue from a suitable solvent.

The coupling of the present active ester obtained above with an alkyl ester of an amino acid or peptide is carried out according to the following procedure: The active oxime ester and an alkyl ester of an amino acid or peptide are dissolved in a nonaqueous solvent such as ethyl acetate, methylene chloride, THF, N',N'-dimethylformamide, or dioxane, and the resulting solution is stirred for several hours or overnight at room temperature to complete the reaction. After completion of the reaction, the solvent is removed by distillation or the reaction mixture is partitioned between water and ethyl acetate or methylene chloride to separate the organic layer. After washing in a customary manner successively with 5-% aqueous citric acid solution, 1-N aqueous sodium hydrogen carbonate solution and water, the reaction product is easily isolated.

The resulting peptide compound is satisfactory in both the optical purity and the yield, indicating that it is effective to use the oxime in the form of active ester according to this invention.

The invention is illustrated below in detail with reference to Examples, but the invention is not limited thereto. All amino acids used in Examples are L-amino acids except for glycine.

EXAMPLE 1

In Table 1 are shown reactivities of oxime esters of this invention with benzylamine in comparison with those of known oxime esters.

TABLE 1

| | Active ester of N—benzyloxycarbonylglycine | |
|---|---|---|
| | Reaction time | |
| Alcohol component | 50% | 80% |
| Oxime ester of present invention: | | |
| 5-Nitro-2-hydroxybenzaldehyde oxime | 30 sec. | 1 min. 6 sec. |
| 5-Nitro-2-hydroxyacetophenone oxime | 52 sec. | 2 min. 25 sec. |
| 5-Nitro-2-hydroxybenzophenone oxime | 35 sec. | 1 min. 35 sec. |
| 5-Chloro-2-hydroxybenzaldehyde oxime | 1 min. | 4 min. |
| 5-Chloro-2-hydroxyacetophenone oxime | 8 min. | 12 min. |
| 5-Chloro-2-hydroxybenzophenone oxime | 5 min. | 8 min. |

TABLE 1-continued

Active ester of N—benzyloxycarbonylglycine

| Alcohol component | Reaction time | |
| --- | --- | --- |
| | 50% | 80% |
| o-Hydroxybenzaldehyde oxime | 1 min. 45 sec. | 4 min. |
| o-Hydroxyacetophenone oxime | 5 min. 15 sec. | 10 min. |
| o-Hydroxybenzophenone oxime | 3 min. 40 sec. | 6 min. |
| Known ester: (for comparison) | | |
| p-Nitrophenol | 3 min. 15 sec. | 5 min. |
| m-Nitroacetophenone oxime | 52 min. | — |
| Acetophenone oxime | 110 min. | — |

The results shown in Table 1 were obtained by the following experimental procedure.

Into a 50-ml flask, was added 2 mmol. of an oxime ester of N-benzyloxycarbonylglycine (or an p-nitrophenol ester) followed by THF to make up to 50 ml. The flask was placed in a thermostat at 30±0.1° C. for 30 minutes to establish constant temperature throughout the flask. Likewise, 4.0 mmol. of benzylamine was made up to 50 ml with THF and kept at constant temperature. The two solutions were combined. After a predetermined time, 10 ml of the reaction mixture was withdrawn with a measuring pipet and diluted with 40 ml of water. The unreacted benzylamine was determined by titration with 0.1N hydrochloric acid using Bromocresol Green as indicator.

From Table 1, it is apparent that the novel acylating agents of the present invention are far superior to the conventionally known compounds and in some cases even superior to p-nitrophenol esters.

When the benzylamine used in the present Example is replaced by an alkyl ester of an amino acid and this alkyl ester is used as the amine component, a peptide can be directly synthesized (see Example 5 and other Examples which follow).

Although stable at room temperature, the present compound (I) is preserved preferably in dark cool place.

EXAMPLE 2

Preparation of 5-nitro-2-hydroxybenzophenone oxime

Into an autoclave, were charged 30 g of 2-chloro-5-nitrobenzophenone, 300 ml of water, and 9.70 g of potassium hydroxide. The mixture was allowed to react at 150° to 160° C. with stirring for 5 hours. Upon cooling to room temperature, there was obtained a clear liquid, reddish orange in color. The liquid was further cooled below 0° C. and strongly acidified with cold concentrated hydrochloric acid. The precipitated solids were collected by filtration, washed with water, and recrystallized from ethanol to yield 15.7 g (56.1%) of 5-nitro-2-hydroxy-benzophenone having a melting point of 122°–123° C. To 150 ml of 40-% aqueous potassium hydroxide solution, was added 25.0 g of 5-nitro-2-hydroxybenzophenone followed by 50 g of hydroxylamine hydrochloride. After 5 hours, the resulting clear liquid was cooled and acidified with concentrated hydrochloric acid to form a precipitate. The precipitate was washed with water and a small volume of 50-% aqueous methanol, then dried in air, and recrystallized from benzene and petroleum ether to yield 5-nitro-2-hydroxybenzophenone oxime.

Yield: 17.1 g (64.4%)

Melting point: 193°–196° C.
Elementary analysis:

| | C % | H % | N % |
| --- | --- | --- | --- |
| Calculated for $C_{13}H_{10}N_2O_4$ | 60.47 | 3.90 | 10.85 |
| Found | 60.38 | 3.85 | 10.76 |

Thin layer chromatography: $R_f=0.78$, as developed with a chloroform-methanol-petroleum ether (95:3:3) mixture.

EXAMPLE 3

Preparation of benzyloxycarbonylglycine 5-nitro-2-hydroxyacetophenone oxime ester Into DMF, were dissolved 9.4 g of benzyloxycarbonylglycine and 8.8 g of 5-nitro-2-hydroxyacetophenone oxime. To the resulting solution cooled to 0° C., was added 9.70 g of dicyclohexylcarbodiimide. After having been left standing for several hours while cooling, the mixture was stirred overnight at room temperature. The precipitated urea derivative was removed by filtration and the filtrate was partitioned between water and ethyl acetate. The ethyl acetate layer was washed with water, dried over magnesium sulfate, and distilled. The residue was recrystallized from ethyl acetate and petroleum ether to yield the intended product. Yield 15.1 g (87.0%); melting point 125°–128° C.

Thin layer chromatography: $R_f=0.87$, as developed with a chloroform-methanol-petroleum ether (95:5:3) mixture.

Elementary analysis:

| | C % | H % | N % |
| --- | --- | --- | --- |
| Calculated for $C_{18}H_{17}N_3O_7$ | 55.82 | 4.42 | 10.85 |
| Found | 56.15 | 4.56 | 10.87 |

EXAMPLE 4

Preparation of benzyloxycarbonylglycine o-hydroxyacetophenone oxime ester

Into 50 ml of dioxane, were dissolved 4.18 g of benzyloxycarbonylglycine and 2.8 ml of triethylamine. To the solution cooled below −10° C., was added dropwise over a period of 5 minutes 2.73 g of isobutyl chloroformate. After one hour, 3.02 g of o-hydroxyacetophenone oxime was added to the mixture. The mixture was stirred at a temperature below −10° C. and then at room temperature overnight. The mixture was then partitioned between ethyl acetate and water. The organic layer was separated and washed thoroughly with 1-N aqueous sodium hydrogen-carbonate solution and water. The organic layer was separated, dried, and distilled. The residue was recrystallized from ethyl acetate and petroleum ether to yield the intended product.

Yield: 3.75 g (55%); melting point 109°–110° C.

$R_f=0.70$, as developed with the same solvent system as used in Example 2.

Elementary analysis:

| | C % | H % | N % |
| --- | --- | --- | --- |
| Calculated for $C_{18}H_{18}N_2O_5$ | 63.15 | 5.30 | 8.18 |
| Found | 63.33 | 5.30 | 8.34 |

EXAMPLE 5

Preparation of N-α-tert-butyloxycarbonyl-N-ε-benzyloxycarbonyl-L-lysylglycine ethyl ester To a solution of 2.77 g of glycine ethyl ester hydrochloride and 2.77 ml of triethylamine in 100 ml of methylene chloride, was added at room temperature 10.0 g of N-α-tert-butyloxycarbonyl-N-ε-benzyloxycarbonyl-L-lysine o-hydroxyacetophenone oxime ester. The mixture was stirred overnight and distilled. The residue was dissolved in 200 ml of ethyl acetate and the resulting solution was thoroughly washed successively with 5-% aqueous citric acid solution, 1-N aqueous sodium hydrogen-carbonate solution, and water. The washed solution was dried over magnesium sulfate and distilled. The residue was recrystallized from ethyl acetate and n-hexane to yield the intended product.

Yield: 7.55 g (83.3%)
Melting point: 51°–53° C.
$[\alpha]_D^{24} = -12.1°$ ($-13.1°$, as found in the literature) (c=1, methanol)
Elementary analysis:

|  | C % | H % | N % |
|---|---|---|---|
| Calculated for $C_{23}H_{35}N_3O_7$ | 59.34 | 7.58 | 9.03 |
| Found | 59.30 | 7.74 | 9.07 |

EXAMPLE 6

Preparation of N-benzyloxycarbonylglycylglycine ethyl ester

Into 70 ml of THF, were added 2.95 g of N-benzyloxycarbonylglycine o-hydroxybenzaldehyde oxime ester and 1.3 g of glycine ethyl ester hydrochloride, followed by 1.3 ml of triethylamine. The mixture was stirred overnight and the reaction mixture was partitioned between water and ethyl acetate. The ethyl acetate layer was separated, washed as in Example 5, dried, and distilled. The solids obtained as the residue were recrystallized from ethyl acetate and petroleum ether to yield the intended product.

Yield: 1.98 g (75.0%)
Melting point: 79°–80° C.
Elementary analysis:

|  | C % | H % | N % |
|---|---|---|---|
| Calculated for $C_{14}H_{18}N_2O_5$ | 57.14 | 6.16 | 9.52 |
| Found | 57.12 | 6.27 | 9.59 |

EXAMPLE 7

Preparation of N-tert-butyloxycarbonylphenylalanylglycine ethyl ester

Into THF, were added 4.43 g of N-tert-butyloxycarbonylphenylalanine 2-hydroxy-5-nitroacetophenone oxime, 1.40 g of glycine ethyl ester hydrochloride, and 1.40 ml of triethylamine. The mixture was allowed to react overnight and the reaction mixture was worked up as in Example 5 to yield the intended product.

Yield: 3.88 g (85.0%)
Melting point: 88°–90° C.
$[\alpha]_D^{20} = -4.6°$ (c=2, ethanol)
Elementary analysis:

|  | C % | H % | N % |
|---|---|---|---|
| Calculated for $C_{18}H_{26}N_2O_5$ | 61.70 | 7.48 | 7.99 |
| Found | 61.53 | 7.59 | 7.88 |

EXAMPLE 8

Preparation of N-benzyloxycarbonylalanylglycine ethyl ester

Into 60 ml of THF, were added 5.14 g of N-benzyloxycarbonylalanine o-hydroxybenzophenone oxime ester and glycine ethyl ester hydrochloride, followed by 1.74 ml of triethylamine. The mixture was worked up as in Example 5 to obtain the intended product.

Yield: 2.80 g (73.9%)
Melting point: 97°–98° C.
$[\alpha]_D^{20} = -21.3°$ (c=1, ethanol)
Elementary analysis:

|  | C % | H % | N % |
|---|---|---|---|
| Calculated for $C_{15}H_{20}N_2O_5$ | 58.43 | 6.54 | 9.09 |
| Found | 58.76 | 6.78 | 9.18 |

EXAMPLE 9

Preparation of N-tert-butyloxycarbonylprolylleucylglycine methyl ester

Into 80 ml of methylene chloride, were dissolved 3.80 g of N-tert-butyloxycarbonylproline 2-hydroxy-5-nitrobenzaldehyde oxime ester, and 2.39 g of leucylglycine methyl ester hydrochloride and 1.4 ml of triethylamine. The mixture was allowed to react overnight. The reaction mixture was concentrated and the residue was transferred into 300 ml of ethyl acetate. The resulting solution was washed successively with 5% aqueous citric acid solution, water, 1-N aqueous sodium hydrogencarbonate solution, and water. The washed solution was dried over magnesium sulfate and distilled. The solids obtained as the residue were recrystallized from ethyl acetate and petroleum ether to yield the intended product.

Yield: 3.26 g (81.7%)
Melting point: 110°–112° C.
$[\alpha]_D^{20} = -83.0°$ (c=1.0, ethanol)
Elementary analysis:

|  | C % | H % | N % |
|---|---|---|---|
| Calculated for $C_{19}H_{33}N_3O_6$ | 57.13 | 8.33 | 10.52 |
| Found | 57.25 | 8.18 | 10.67 |

What is claimed is:

1. A acylation process which comprises using as the acylating agent an o-hydroxy-substituted aromatic oxime ester represented by the general formula (I)

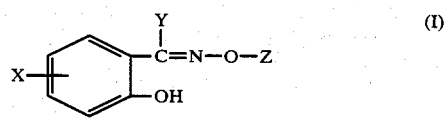

wherein X represents H, Cl, $NO_2$, $CO_2C_2H_5$, $CO_2CH_3$, $CONH_2$ or CN, Y represents H, $CH_3$, or $C_6H_5$, and Z represents an acyl group represented by the general formula (II)

(II)

where $R_1$ represents H, $C_{1-10}$ alkyl, allyl, aralkyl, N-protected amino acid moiety, or a peptide comprising protected amino acids; and mixing said acylating agent with an amine substance represented by the general formula (III)

(III)

wherein $R_2$ represents H, straight chain or branched chain $C_{1-5}$ alkyl,

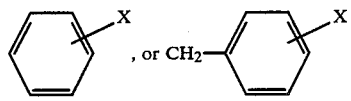

where X is as defined above and T represents $C_{1-10}$ alkyl, allyl, aralkyl, amino acid moiety with a protected acid component, or a peptide comprising protected amino acids to form a compound represented by the general formula (IV)

(IV)

wherein $R_2$, Z and T are as defined above.

2. The acylation process of claim 1, wherein X is hydrogen.

3. The acylation process of claim 1, wherein X is chlorine.

4. The acylation process of claim 1, wherein X is a nitro group.

5. The acylation process of claim 3, wherein the X is in the 5 position on the benzene ring.

6. The acylation process of claim 4, wherein the X is in the 5 position on the benzene ring.

7. The acylation process of claim 1, wherein the oxime ester is 5-nitro-2-hydroxybenzaldehyde oxime.

8. The acylation process of claim 1, wherein the oxime ester is 5-nitro-2-hydroxyacetophenone oxime.

9. The acylation process of claim 1, wherein the oxime ester is 5-nitro-2-hydroxybenzophenone oxime.

* * * * *